United States Patent [19]

Bush et al.

[11] Patent Number: 4,568,675

[45] Date of Patent: Feb. 4, 1986

[54] PHENAZINE ACE INHIBITOR PRODUCED FROM STREPTOMYCES SPECIES

[75] Inventors: Karen Bush, Kingston; Dorothy S. Slusarchyk, Belle Mead; Wen-Chih Liu, Princeton Junction, all of N.J.

[73] Assignee: E. R. Squibb & Sons, Inc., Princeton, N.J.

[21] Appl. No.: 562,914

[22] Filed: Dec. 19, 1983

[51] Int. Cl.$^4$ .................. C07D 241/46; A61K 31/495
[52] U.S. Cl. ..................... 514/250; 435/146; 544/347
[58] Field of Search .................. 544/347; 514/250

[56] References Cited

PUBLICATIONS

Römer, A. I Budzikiewicz, H., Korth, H. & Pulver, G.: Neue Phenazinderivate aus *Pseudomonas aureofaciens*, Tetrahedron Letters, 1979: pp. 509–512.
Gerber, N. N.: New Microbial Phenazines (1), Journal of Heterocyclic Chemistry 6: pp. 297–300, 1969.
Römer, A. II Scholl, H., Budzikiewicz, H., Korth, H., Pulver, G.: Phenazine aus Pseudomonaden, Z. Naturforsch 36b: pp. 1037–1046, 1981.

*Primary Examiner*—Mark L. Berch
*Attorney, Agent, or Firm*—Lawrence S. Levinson; Donald J. Barrack

[57] ABSTRACT

3,6-Dihydroxyphenazine-1-carboxylic acid, a hypotensive agent, and its production by culturing aerobically Streptomyces species A.T.C.C. No. 39460 are disclosed herein.

2 Claims, No Drawings

PHENAZINE ACE INHIBITOR PRODUCED FROM STREPTOMYCES SPECIES

SUMMARY OF THE INVENTION

Cultivation of a strain of a microorganism identified as a Streptomyces species belonging to the *Streptomyces tanashiensis-zaomyceticus* group, which has been deposited in the American Type Culture Collection as A.T.C.C. No. 39460, yields the novel chemical substance which has been designated EM5523.

EM5523 has been analyzed and found to be 3,6-dihydroxyphenazine-1-carboxylic acid, a compound having the formula

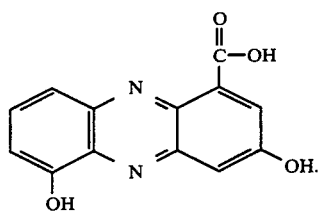

EM5523, and pharmaceutically acceptable salts thereof, are hypotensive agents. They inhibit the conversion of the decapeptide angiotensin I to angiotensin II and, therefore, are useful in reducing or relieving angiotensin related hypertension. The action of the enzyme renin·on angiotensinogen, a pseudoglobulin in blood plasma, produces angiotensin I. Angiotensin I is converted by angiotensin converting enzyme (ACE) to angiotensin II. The latter is an active pressor substance which has been implicated as the causative agent in several forms of hypertension in various mammalian species, e.g., humans. EM5523 intervenes in the angiotensinogen→(renin)→angiotensin I→(ACE)→angiotensin II sequence by inhibiting angiotensin converting enzyme and reducing or eliminating the formation of the pressor substance angiotensin II. Thus by the administration of a composition containing one (or a combination) of the compounds of this invention, angiotensin dependent hypertension in a species of mammal (e.g., humans) suffering therefrom is alleviated. A single dose, or preferably two to four divided daily doses, provided on a basis of about 1.0 to 100 milligrams per kilogram of body weight per day, preferably about 1 to 15 milligrams per kilogram of body weight per day, is appropriate to reduce blood pressure. The substance is administered parenterally.

The expression "pharmaceutically acceptable salt" refers to basic salts formed with inorganic and organic bases. Such salts include ammonium salts, alkali metal salts like sodium and potassium salts (which are preferred), alkaline earth metal salts like the calcium and magnesium salts, salts with organic bases, e.g., dicyclohexylamine salt, benzathine, N-methyl-D-glucamine, hydrabamine salts, salts with amino acids like arginine, lysine and the like.

The salts are formed in a conventional manner by reacting the free acid form of the product with one or more equivalents of the appropriate base providing the desired cation in a solvent or medium in which the salt is insoluble, or in water and removing the water by freeze drying. By neutralizing the salt with an insoluble acid like a cation exchange resin in the hydrogen form (e.g., polystyrene sulfonic acid resin like Dowex 50) or with an aqueous acid and extraction with an organic solvent, e.g., ethyl acetate, dichloromethane or the like, the free acid form can be obtained, and, if desired, another salt formed.

DETAILED DESCRIPTION OF THE INVENTION

The Microorganism

The organism used to produce 3,6-hydroxyphenazine-1-carboxylic acid is a strain of a Streptomyces species belonging to the *Streptomyces tanashiensis-zaomyceticus* group isolated from soil. A subculture of the organism may be obtained from the American Type Culture Collection. Rockville, Md. Its accession number in the repository is A.T.C.C. No. 39460.

The species in the *Streptomyces tanashiensis-zaomyceticus* group cannot be differentiated from one another within the framework of the existing classification in Bergey's Manual, 8th edition.

The characteristics of the Streptomyces species A.T.C.C. No. 39460 are:

The organism produces both vegetative and aerial mycelium. The aerial mycelium bears straight chains of spores (Rectus flexibilis group). The spore surface is smooth by transmission electron microscopy.

The spore color on oatmeal agar is light brownish gray corresponding to Color Harmony Manual chip No. 3 fe (ISCC-NBS#63). The reverse is brownish gray CHM-No. 4 li (ISCC-NBS#64). Melanoid pigment is produced on the tyrosine medium of Arai and Mikami: *Appl. Microbiol* 23:402 (1972).

The carbon utilization pattern after the method of Pridham & Gottlieb (1948, J. Bacteriol, 56 (1):107–114) indicates that glucose, xylose and arabinose are utilized as sole carbon sources; rhamonose, fructose, raffinose, mannitol, inositol and sucrose are not.

For isolating the organism, a portion of a soil sample containing the organism is stamped onto an agar of the following compositions:

Glycerol 12.6 ml
Citric acid 1.2 gm
$(NH_4)_2HPO_4$ 0.4 gm
KCl 0.08 gm
$MgCl_2.6H_2O$ 0.418 gm
$MnCl_2.4H_2O$ 0.036 gm
$FeSO_4.7H_2O$ 0.023 gm
$ZnCl_2.6H_2O$ 0.021 gm
$CoCl_2.6H_2O$ 0.004 gm
Agar 15.0 gm
Distilled water to 1000 ml The medium is adjusted to pH about 7.2 and sterilized in an autoclave at 121° C. for 30 minutes. After 4 to 7 days incubation at 25° C., the colonies of Streptomyces species A.T.C.C No. 39460 are isolated from the plated soil. The isolated colonies are picked off and maintained on an agar medium composed of:

|  | Grams |
| --- | --- |
| Yeast extract | 1.0 |
| Beef extract | 1.0 |
| NZ Amine A | 2.0 |
| Glucose | 10.0 |
| Agar | 15.0 |
| Distilled water to | 1000 ml |

The medium is adjusted to pH about 7.3 and sterilized in an autoclave at 121° C. for 15 minutes.

Biological Production of EM5523

Streptomyces species A.T.C.C. No. 39460 produces EM5523 which possesses angiotensin converting enzyme inhibitory activity. To form EM5523 according to the preferred methodology of this invention, Streptomyces species A.T.C.C. No. 39460 is grown at, or near, room temperature (25° C.) under submerged aerobic conditions in an aqueous nutrient medium containing an assimilable carbohydrate and nitrogen source. The fermentation is carried out for approximately 120 hours, at the end of which time EM5523 has been formed.

After the fermentation is complete, cells are removed by centrifugation and EM5523 is extracted into n-butanol at pH 2 and back into water at pH 9. The solution is neutralized, concentrated, and the resulting crude EM5523 further purified by partition chromatography on cellulose, eluting with ethyl acetate and by reverse phase chromatography on macroreticular polystyrene resins, eluting with gradients of methanol in water.

Synthetic Production of EM5523

EM5523 can also be prepared by organic synthesis. An exemplary process comprises first reacting 4-methoxy-2-methylaniline with o-Nitroanisole to yield 3,5-dimethoxy-1-methylphenazine. Conversion of 3,5-dimethoxy-1-methylphenazine to 6-methyl-1,8-phenazinediol can be accomplished by refluxing the phenazine in benzene in the presence of aluminum trichloride.

Protection of the hydroxy groups of 6-methyl-1,8-phenazinedoil (e.g., by reaction with bromomethyl methyl ether) followed by bromination of the 6-methyl substituent (e.g., by reaction with N-bromosuccinimide) yields 6-bromomethyl-1,8-di-(methoxymethoxy)phenazine. Conversion of the bromomethyl group to a formyl group (e.g., by treatment with silver fluoroborate), followed by oxidation of the formyl group to a carboxyl group (e.g., by treatment with silver oxide and sodium cyanide) and deprotection of the hydroxy groups yields the desired 3,6-dihydroxyphenazine-1-carboxylic acid.

EXAMPLE OF FERMENTATION OF STREPTOMYCES SPECIES A.T.C.C. No. 39460

Streptomyces species A.T.C.C. No. 39460 was maintained on the following sterilized agar medium(A):

|  | Grams |
| --- | --- |
| Yeast extract | 1.0 |
| Beef extract | 1.0 |
| NZ Amine A | 2.0 |
| Glucose | 10.0 |
| Agar | 15.0 |
| Distilled water to | 1000 ml |

The pH was adjusted to 7.3 before sterilization at 121° C. for 30 minutes.

A loopful of surface growth from an agar slant (Medium A) of Streptomyces species A.T.C.C. No. 39460 was used to inoculate each of twenty 500 ml Erlenmeyer flasks, containing 100 ml each of the following sterilized medium (B):

|  | Grams |
| --- | --- |
| Yeast extract | 4.0 |
| Malt extract | 10.0 |
| Dextrose | 4.0 |
| Distilled water to | 1000 ml |

The pH was adjusted to 7.3 before sterilization at 121° C. for 15 minutes.

After inoculation, the flasks were incubated at 25° C. on a rotary shaker (300 rpm; 2 inch stroke) for 72 hours. After the appropriate incubation as described above, 5% (vol/vol) transfers were made from the grown culture flasks to four hundred 500 ml Erlenmeyer flasks containing 100 ml each of the following sterilized medium (C):

|  | Grams |
| --- | --- |
| Citric acid | 12.8 |
| $(NH_4)_2SO_4$ | 6.0 |
| $MgSO_4.7H_2O$ | 0.25 |
| $KH_2PO_4$ | 0.15 |
| $MnSO_4.4H_2O$ | 0.01 |
| $CaCO_3$ | 11.0 |
| Glucose | 20.0 (Sterilized separately) |
| Distilled water to | 1000 ml |

Sterilization was at 121° C. for 15 minutes.

After inoculation, the flasks were incubated at 25° C. on a rotary shaker (300 rpm; 2 inch stroke) for 120 hours. At this time, the contents of the flasks were pooled, the broth was centrifuged, and the supernate (36 liters) was adjusted to pH 2 with hydrochloric acid. The resulting solution was extracted with two 18 liter portions of n-butanol. The combined butanol exacts were mixed with 18 liters of water and adjusted to pH 9 with sodium hydroxide. The aqueous layer was separated. adjusted to pH 7 with hydrochloric acid, concentrated to 1 liter and freeze dried.

A cellulose partition chromatography column was prepared by mixing 250 g of Whatman CF11 cellulose powder with 45 ml of ethyl acetate-saturated water and packing the wet cellulose in water-saturated ethyl acetate. The freeze dried solid was dissolved in 100 ml of ethyl acetate-saturated water, adjusting the pH to 5.5. The solution was mixed with 10 g of cellulose powder, slurried with 120 ml of water-saturated ethyl acetate, and the slurry was applied to the column. The column was then eluted with water-saturated ethyl acetate until the activity emerged. ACE inhibition was determined spectrophotometrically using p-nitrobenzyloxycarbonylglycyl (S-4-nitrobenzo-2-oxa-1,3-diazole)-L-cysteinylglycine as the chromogenic substrate and partially purified rabbit lung ACE as enzyme; captopril was used as a positive standard. Active fractions were combined and concentrated to dryness, giving 1.92 g of residue. This was dissolved in 40 ml of water, adjusting the pH to 7.4 with sodium hydroxide. The solution was applied to a 2.5×40 cm column of 75 to 150 micron MCI gel CHP20P* packed in water. The column was eluted with a linear gradient prepared from 550 ml of water and 550 ml of methanol. Active fractions were combined and concentrated, giving 123 mg of residue. The residue was dissolved in 10 ml of water at pH 7 and applied to a 2.5 cm×18 cm column of 75 to 150 micron Servachrom XAD-2** and eluted with a gradient of methanol in water as above. Active fractions were combined and concentrated, giving 36 mg of EM5523, sodium salt. The salt was dissolved in 8 ml of water and the solution adjusted to pH 5.1 with hydrochloric acid. A small amount of dry Servachrom XAD-2 was added and the resulting mixture applied to a 2.5×15 cm column of Servachrom XAD-2 packed in water. The column was eluted with a linear gradient prepared from 250 ml each of water and methanol. The most active fractions were combined and upon concentration gave 2.2 mg of EM5523 (free acid) as fine orange needles; melting point >310° C.; UV max in methanol (E¹%) 218 (200), 268 (840), 385 (80), 460 nm (sh); UV max is acidified methanol 215, 268, 395, 466 nm; IR (KBr) 3330, 1694, 1620, 1598, 1568, 1472, 1415, 1385, 1320, 1268, 1171, 1087, 751 cm$^{-1}$; mass spectrum (M+) 256; TLC (silica gel, methanol-chloroform, 1:9) $R_f$ 0.63.

*MCI gel CHP20P is a styrene-divinylbenzene copolymer in bead form having a macroreticular structure (Mitsubishi Chemical Industries, Ltd.)
** Servachrom XAD-2 is a macroreticular crosslinked polystyrene resin available from Serva, Heidelberg, Germany (distributed in the U.S.A. by Accurate Chemical Scientific Corp., Hicksville, NY).

| Electrophoresis* of EM5523 | | |
|---|---|---|
| System | pH | Mobility** |
| Formic acid-acetic acid-water, 1:3:36 | 1.8 | 0 |
| 0.05 M sodium phosphate | 4.5 | 0 |
| Sodium 0.05 M phosphate | 7.0 | 0.34 |
| Sodium 0.05 M carbonate-bicarbonate | 9.2 | 0.89 |

*12 Vcm$^{-1}$, 1 hr., Whatman No. 2 paper
**Relative to vitamin B$_{12}$ (0.0) and p-nitrobenzenesulfonate (1.00).

EXAMPLE OF ORGANIC SYNTHESIS OF EM5523

(A) 3,6-Dimethoxy-1-methylphenazine

A mechanically stirred mixture of 66.0 ml (0.51 mol) of freshly distilled 4-methoxy-2-methylaniline, 50.5 ml (0.41 mol) of freshly distilled o-nitroanisole, 189 g (3.37 mol) of finely powdered potassium hydroxide, and 945 ml of toluene was heated to reflux (initially exothermic) for 1 hour. The mixture was then cooled to room temperature, filtered, and the filter cake washed with toluene, 1% methanol/dichloromethane, and dichloromethane. The solvent from the combined filtrate and washings was removed in vacuo to yield 86 g of black solid. The black material was then flash filtered through silica gel eluting with ether and the fractions containing the desired phenazine ($R_f$=0.22 on silica gel, dichloromethane) were combined, concentrated in vacuo and purified by flash chromatography, eluting with dichloromethane. A final chromatography on a Waters Prep-500 chromatograph (6:1 hexane-acetone) followed by recrystallization from a hexane/toluene mixture afforded 12.3 g of the title compound as yellow needles, melting point 201°–202° C.

(B) 6-Methyl-1,8-phenazinediol

A magnetically stirred mixture of 0.509 g (2 mmol) of 3.6-dimethoxy-1-methylphenazine, 1.0 g of aluminum trichloride (7.5 mmol), and 20 ml of benzene was heated at reflux for 18 hours. The mixture was cooled to room temperature and the solvent was removed on a rotary evaporator. The residue was treated with crushed ice and the resulting mixture was taken up in 1N sodium hydroxide and washed with dichloromethane. The combined dichloromethane layers were back-extracted with 1N sodium hydroxide and the combined aqueous layers were acidified to pH 4–5. The solution was extracted with dichloromethane containing a trace of methanol. The combined organic layers were washed with brine and dried over magnesium sulfate. The solvent was was stripped to yield 1.06 g of a brown and yellow solid mixture. Flash chromatography in 6:1 toluene-acetone yielded 0.38 g of a yellow solid. This was recrystallized from toluene to yield 298 mg of orange crystals; decomposition at >256° C.

(C) 6-Methyl-1,8-di(methoxymethoxy)phenazine

A stirred suspension of 6-methyl-1,8-phenazinediol (113 gm, 0.5 mM), finely ground potassium carbonate (690 gm, 5.0 mM) and 18-Crown-6 (catalytic amount) in anhydrous tetrahydrofuran (4 ml) was cooled to 0° C. (ice bath) and treated with bromomethyl methyl ether (156 mg, 1.25 mM) (dropwise addition on large scale) under argon atmosphere. After stirring at 0° C. for 30 minutes, the reaction was allowed to warm up to room temperature and stirring continued for 5 hours. The suspension was filtered through a Celite pad and the solid washed with chloroform. Solvent evaporation provided yellow solid which was recrystallized from dichloromethane ether to give yellow needles (119 mg). The mother liquor was purified by preparative TLC (1% methanol in dichloromethane) to give 11 gm of additional product. Combined yield, 130 mg, melting point 157°–158° C. from dichloromethane ether.

(D) 6-Bromomethyl-1,8-di(methoxymethoxy)phenazine

The reaction mixture containing 6-methyl-1,8-di(methoxymethoxy)phenazine (188 mg, 0.6 mM), recrystallized N-bromosuccinimide (120 mg, 0.7 mM) and azobisisobbutyronitrile (5 mg 0.03 mM) in carbon tetrachloride (6 ml, dried over alumina) was heated under reflux in an argon atmosphere while shining light on it using a sun lamp. After one hour, the reaction was cooled to room temperature, diluted with dichloromethane and washed with water. After drying over anhydrous magnesium sulfate, the solvent was stripped off to give a brown residue. Purification by flash chromatography on silica gel (Whatman LPS-1) using dichloromethane as eluent provided the crystalline title compound (127 mg), (melting point 167°–168° C. from dichloromethane-ether) along with recovered starting material (20 mg).

(E) 6-Formyl-1,8-di(methoxymethoxy)phenazine

To a solution of silver fluoroborate (359 mg, 1.86 mM) in anhydrous dimethylsulfoxide (15 ml) was added 6-bromomethyl-1,8-di(methoxymethoxy)phenazine (600 mg, 1.53 mM) and the resulting suspension was stirred overnight at room temperature under an argon atmosphere. It was then treated with triethylamine (0.5 ml) and the stirring continued for 30 more minutes. The reaction was diluted with dichloromethane and filtered through Celite. The filtrate was thoroughly washed with water, brine and dried over anhydrous magnesium sulfate. Evaporation under reduced pressure provided yellow solid which was taken up in dry dichloromethane (5 ml) and added to a solution of pyridinium chlorochromate (130 mg, 0.6 mM) in the same solvent (2 ml). After stirring for 3 hours, the reaction was worked up in a standard fashion (ether quench) to give orange solid. Purification by flash chromatography on silica gel (Whatman LPS-1) using chloroform as eluent gave the title compound (406 mg) as yellow needles, melting point 148°–150° C. from chloroform-ether.

(F) 6-Carboxyl-1,8-di(methoxymethoxy)phenazine

A suspension of 6-formyl-1,8-di(methoxymethoxy)-phenazine (400 gm, 1.22 mM) and silver oxide (1.6 g, 13 mM) in methanol (30 ml) was treated with sodium cyanide (300 mg, 6.1 mM) and the reaction mixture heated (85° C. oil bath temp.) under argon for 6 hours. The reaction mixture was allowed to cool down to room temperature and was then filtered through a Celite pad. The filtrate was evaporated down to 20 ml volume and treated with 2N potassium hydroxide (6 ml) (in order to hydrolyze the ester formed). After stirring it at room temperature for 1–2 hours, the reaction mixture was diluted with water (20 ml) and excess methanol was removed under reduced pressure. The resulting aqueous solution was stirred with chloroform, and 2N hydrochloric acid was carefully added to the two-phase solution until the pH approached ~3. The organic layer was separated, the aqueous phase was reextracted with chloroform. The combined extracts were washed with brine, dried over magnesium sulfate and evaporated to give yellow solid. Recrystallization from chloroform-ether provided the title compound (320 mg) as yellow needles. The mother liquor was purified by preparative TLC on silica gel (2% methanol in dichloromethane, run twice) to give 10 more mg of the product. Combined yield, 330 mg; melting point 178°–180° C. from chloroform-ether.

(G) 3,6-Dihydroxyphenazine-1-carboxylic acid

A solution of 6-carboxyl-1,8-di(methoxymethoxy)-phenazine (327 gm, 0.96 mM) in tetrahydrofuran (15 ml) and 70% trifluoroacetic acid (20 ml) was stirred at room temperature for 5 hours and then heated at 70° C. for 2 hours. It was cooled to ambient temperature, diluted with water (10 ml), and the solvent was evaporated in vacuo to give a yellow residue which was suspended in acetone-ether (1:2) and filtered off. The solid was washed with the same solvent mixture and dried under vacuum at 50° C. for 10 hours to give the title compound (240 mg), melting point >300° C.

What is claimed is:

1. 3,6-Dihydroxyphenazine-1-carboxylic acid, or a pharmacetically acceptable basic salt thereof.

2. A method of lowering blood pressure in a mammal in need thereof, which comprises administering to said mammal an effective amount of 3,6-dihydroxyphenazine-1-carboxylic acid, or a pharmaceutically acceptable basic salt thereof.

* * * * *

UNITED STATES PATENT AND TRADEMARK OFFICE
CERTIFICATE OF CORRECTION

PATENT NO. : 4,568,675

DATED : February 4, 1986

INVENTOR(S) : Karen Bush et al.

It is certified that error appears in the above-identified patent and that said Letters Patent is hereby corrected as shown below:

Column 1, line 46, "1.0" should be --0.1--.

Column 3, line 30, "phenazinedoil" should be --phenazinediol--.

Column 5, line 62, "The" should be --This--.

Column 6, line 19 "gm" should be --mg--.

Signed and Sealed this

Fourteenth Day of October, 1986

[SEAL]

Attest:

DONALD J. QUIGG

*Attesting Officer*  *Commissioner of Patents and Trademarks*